(12) United States Patent
Kokish et al.

(10) Patent No.: US 7,448,122 B1
(45) Date of Patent: Nov. 11, 2008

(54) METHOD OF COMPRESSING A POLYMERIC LAYER OF AN EXPANDABLE MEDICAL DEVICE

(75) Inventors: Arkady Kokish, Los Gatos, CA (US); Steven Nelson, Scotts Valley, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 900 days.

(21) Appl. No.: 10/698,929

(22) Filed: Oct. 31, 2003

(51) Int. Cl.
*B23P 11/02* (2006.01)
*A61F 2/06* (2006.01)

(52) U.S. Cl. .............................. 29/450; 29/446; 29/451; 623/1.15

(58) Field of Classification Search .................. 29/450, 29/446, 451; 623/1.15
See application file for complete search history.

(56) References Cited

U.S. PATENT DOCUMENTS

| | | | |
|---|---|---|---|
| 3,650,644 A * | 3/1972 | Ebert et al. ..................... 425/66 |
| 4,174,543 A | 11/1979 | Kelman |
| 4,655,769 A | 4/1987 | Zachariades |
| 4,955,899 A * | 9/1990 | Della Corna et al. ....... 623/1.46 |
| 5,374,473 A | 12/1994 | Knox et al. |
| 5,376,110 A * | 12/1994 | Tu et al. ....................... 600/36 |
| 5,433,909 A * | 7/1995 | Martakos et al. ......... 264/209.1 |
| 5,628,786 A | 5/1997 | Banas et al. |
| 5,662,622 A * | 9/1997 | Gore et al. .................... 604/526 |
| 5,711,909 A * | 1/1998 | Gore et al. .................... 264/320 |
| 5,752,934 A | 5/1998 | Campbell et al. |
| 5,788,626 A | 8/1998 | Thompson |
| 5,868,704 A | 2/1999 | Campbell et al. |
| 6,016,848 A | 1/2000 | Egres, Jr. |
| 6,039,755 A * | 3/2000 | Edwin et al. ................ 623/1.15 |
| 6,120,477 A | 9/2000 | Campbell et al. |
| 6,267,834 B1 * | 7/2001 | Shannon et al. ................ 156/84 |
| 6,375,637 B1 | 4/2002 | Campbell et al. |
| 6,428,506 B1 | 8/2002 | Simhambhatla et al. |
| 6,451,047 B2 * | 9/2002 | McCrea et al. .............. 623/1.13 |
| 6,602,224 B1 | 8/2003 | Simhambhatla et al. |
| 6,863,757 B1 | 3/2005 | Gonzalez et al. |
| 7,147,817 B1 * | 12/2006 | Lim et al. ................. 264/289.6 |
| 2004/0061261 A1 * | 4/2004 | Gonzalez et al. ............ 264/403 |

FOREIGN PATENT DOCUMENTS

WO          WO 97/02791          1/1997

* cited by examiner

*Primary Examiner*—Essama Omgba
(74) *Attorney, Agent, or Firm*—Fulwider Patton LLP

(57) ABSTRACT

A method of making a polymeric tubular layer of an expandable medical device or component, in which the polymeric tubular layer is longitudinally compressed by longitudinally stretching a tube over the polymeric tubular layer and releasing the tube from the stretched configuration so that the length of the tube decreases and thereby decreases the length of the polymeric tubular layer. The resulting compressed polymeric tubular layer can be used in a variety of expandable medical devices and in one presently preferred embodiment it forms a catheter balloon having at least one layer.

14 Claims, 4 Drawing Sheets

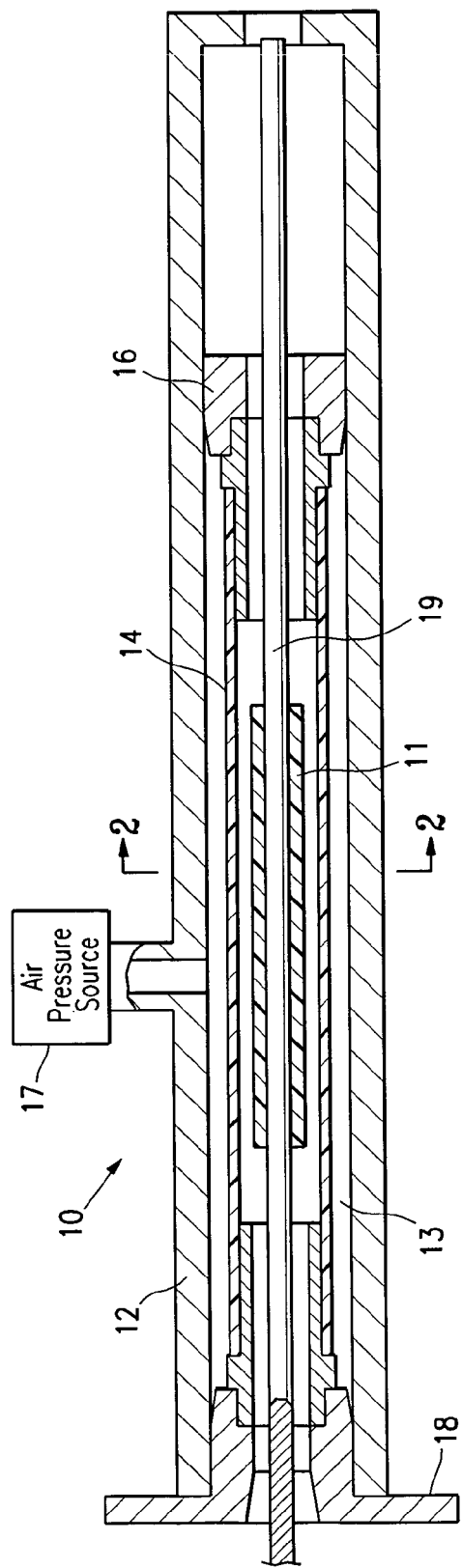
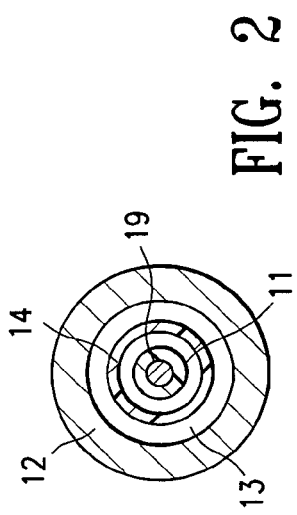
FIG. 1
FIG. 2

METHOD OF COMPRESSING A POLYMERIC LAYER OF AN EXPANDABLE MEDICAL DEVICE

BACKGROUND OF THE INVENTION

This invention generally relates to medical devices, and particularly to intracorporeal devices for therapeutic or diagnostic uses such as balloon catheters, stent covers, and vascular grafts.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g., greater than 8 atmospheres) so that the stenosis is compressed against the arterial wall to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e., reformation of the arterial blockage, which necessitates either another angioplasty procedure or some other method of repairing or strengthening the dilated area. To reduce the restenosis rate and strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to an angioplasty balloon catheter, and expanded to a larger diameter by expansion of the balloon. The balloon is deflated to remove the catheter and the stent left in place within the artery at the site of the dilated lesion. Stent covers commonly provided on an inner or an outer surface of the stent have been used in, for example, the treatment of pseudoaneurysms and perforated arteries and to prevent prolapse of plaque, and generally comprise a cylindrical tube of synthetic or natural material. Similarly, vascular grafts comprising cylindrical tubes commonly made from tissue or synthetic materials such as polyester, expanded polytetrafluoroethylene, and DACRON, are configured to be implanted in vessels to strengthen or repair the vessel, or used in an anastomosis procedure to connect vessel segments together.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed-in-place balloons, that are not folded prior to inflation, but which instead readily expand to the working diameter within the patient's body lumen from a generally cylindrical or tubular shape that conforms to the catheter shaft (i.e., with essentially no folded wings).

Catheter balloons formed of expanded polytetrafluoroethylene (ePTFE) expanded in place within the patient's body lumen without blow molding the ePTFE tubing have been disclosed. Prior disclosed methods of forming the ePTFE balloon involve wrapping a sheet of ePTFE on a mandrel and then heating the wrapped sheet to fuse the layers of wrapped material together. However, one difficulty has been further processing the resulting ePTFE tube after the layers of wrapped material are fused together.

SUMMARY OF THE INVENTION

The invention in directed to a method of making a polymeric tubular layer of an expandable medical device or component, in which the polymeric tubular layer is longitudinally compressed by longitudinally stretching a tube over the polymeric tubular layer and then releasing the tube from the stretched configuration so that the length of the tube decreases and thereby decreases the length of the polymeric tubular layer. The resulting compressed polymeric tubular layer can be used in a variety of expandable medical devices or components thereof, and in one presently preferred embodiment it forms a catheter balloon having at least one layer.

In a presently preferred embodiment, the method of the invention generally comprises placing a polymeric tubular layer having a length in a lumen of a tube, with the polymeric tubular layer being disposed on a mandrel. The tube is longitudinally stretched to a stretched configuration and restrained in the stretched configuration, and the tube in the stretched configuration is attached to the polymeric tubular layer. Unrestraining the tube to release the tube from the stretched configuration causes the length of the tube to decrease, and thereby longitudinally compresses the polymeric tubular layer. The tube is then detached from the compressed polymeric tubular layer, and the compressed polymeric tubular layer removed from the lumen of the tube and from the mandrel, to form the polymeric tubular layer of the expandable medical device. The tube may be stretched, attached to the polymeric tubular layer, and released from the stretched configuration once or multiple times, to thus compress the polymeric tubular layer in one or more cycles, to produce a completed compressed polymeric tubular layer having a desired percent compression.

The stretched configuration of the tube is formed by pulling the tube at one or both ends. The tube preferably stretches uniformly along its length. As a result, as the tube retracts lengthwise from the stretched configuration to a relaxed configuration, it preferably compresses the polymeric tubular layer in a uniform manner. Thus, the method of the invention provides uniform longitudinal compression which is controllable and repeatable. The resulting uniformly compressed polymeric tubular layer has a percent compression which depends on variables such as the number of compression cycles performed, the nature of the polymer(s) forming the tube, and the degree to which the tube is stretched. The resulting amount of longitudinal compression produced in the polymeric tubular layer is expressed herein as a percentage length reduction. Thus, a polymeric tubular layer having a 2 cm precompression length (i.e., the length of the polymeric tubular layer just prior to being longitudinally compressed in accordance with the invention), which is subsequently longitudinally compressed to a length of 1 cm, has a longitudinal compression of 50% (i.e., (2 cm−1 cm)÷2 cm). In one embodiment, the percent compression of the compressed polymeric tubular layer is about 30% to about 65%, and more preferably about 50% to about 60%.

The tube is preferably formed of an elastomeric polymer, although a variety of suitable polymers may be used including nonelastomeric polymers. Preferably, the tube is formed of a polymer having a relatively high resistance in the axial (longitudinal) direction. For example, in one embodiment, the polymeric material forming the tube has a relatively high young's modulus in the axial direction. The high axial direction resistance provides sufficient force during lengthwise retraction from the stretched configuration to longitudinally compress the polymeric tubular layer. Although a presently preferred tube is formed of a polymer having a relatively axial direction resistance or high axial young's modulus, the method variables can be selected depending on the axial direction resistance of the tube to produce the desired percent compression in the final compressed polymeric tubular layer. For example, increasing the degree to which the tube is stretched and the number of compression cycles will increase the percent compression produced by a tube having a relatively low resistance in the axial direction.

The tube is attached to the polymeric tubular layer after being longitudinally stretched, so that as the stretched tube retracts it will longitudinally compress the polymeric tubular layer. Attaching the tube in the stretched configuration to the polymeric tubular layer typically comprises forcing the tube radially inwardly against the polymeric tubular layer, to provide an interference fit (i.e., frictional engagement) between the tube and the polymeric tubular layer. In one embodiment, the tube has a relatively low radial resistance (or for example in one embodiment a low young's modulus in the radial direction), to thereby facilitate pressing the tube radially down onto the polymeric tubular layer. However, the tube's resistance in the radial direction does not have to be relatively low so long as it can be overcome by the force applied to attach the tube in the stretched configuration to the polymeric tubular layer. Thus, in an alternative embodiment, the tube has a relatively high resistance in both the radial and axial direction, although the radial resistance is such that the tube can still be forced radially inwardly against the polymeric tubular layer.

In a presently preferred embodiment, releaseably attaching the tube in the stretched configuration to the polymeric tubular layer comprises exposing the tube with the polymeric tubular member therein to a pressurized fluid such as pressurized air or liquid, to thereby apply a radially inward force to the tube. The tube with the polymeric tubular layer therein is typically in an interior chamber of a housing having a port configured for delivering the pressurized fluid into the interior chamber of the housing, so that the housing at least partially retains the pressurized fluid, and thus allows the pressurized fluid to apply a radially inward force to the tube. However, a variety of suitable methods can be used to releaseably attach the stretched tube to the polymeric tubular layer.

The pressurized fluid enhances the grip between the tube and the polymeric tubular layer to releaseably attach the two together, and causes the tube to radially restrain the polymeric tubular layer therein. The pressurized fluid is therefore preferably delivered at a pressure which is sufficiently high to radially restrain the polymeric tubular member during the longitudinal compression, which thereby prevents or inhibits wrinkles in the compressed polymeric tubular member. The required pressure will depend on factors such as the nature of the polymer(s) forming the tube, and the nature of the polymeric tubular layer. Thus, although the tube in one embodiment is formed of a polymer having a relatively low resistance in the radial direction, a variety of suitable modulus materials may be used for the tube, and the fluid pressure suitably adjusted to provide the desired radial restraining force on the polymeric tubular layer. For example, in order to press a tube formed of a polymer having a relatively high resistance in the radial direction (e.g., a relatively high radial young's modulus), the pressure of the pressurized fluid is increased to a suitably higher pressure than is required for a polymer tube having a lower resistance in the radial direction.

In a presently preferred embodiment, the tube can be repeatedly longitudinally stretched a large number of times, so that the compression assembly can be used repeatedly before the tube has to be replaced. Thus, a single tube can be used not only to repeatedly compress a first polymeric tubular layer, but also to compress a large number of additional samples thereafter. The life span of the tube is a function of the nature of the polymer of the tube as well as the number of times it is stretched and the degree to which it is stretched each time.

The compressed polymeric tubular layer can be used to form a layer of a single or multilayered expandable medical device. In a presently preferred embodiment, the expandable medical device or medical device expandable component is an inflatable balloon for a catheter. A balloon formed according to the method of the invention can be used on a variety of suitable balloon catheters including coronary and peripheral dilatation catheters, stent delivery catheters, drug delivery catheters and the like. Although discussed below primarily in terms of the embodiment in which the medical device tubular component is an inflatable member such as a balloon for a catheter, it should be understood that other expandable medical devices and components are included within the scope of the invention including stent covers and vascular grafts.

The method of the invention provides a compressed polymeric tubular layer for an expandable medical device, preferably having a uniform compression. Moreover, the method facilitates forming a repeatable, controllable, high percent compression, yet without wrinkles in the resulting highly compressed polymeric tubular layer. These and other advantages of the invention will become more apparent from the following exemplary figures and detailed description.

BRIEF DESCRIPTION OF THE DRAWINGS

FIG. 1 illustrates a longitudinal cross section of a compression assembly useful in a method embodying features of the invention, having a polymeric tubular layer positioned in a lumen of a tube.

FIG. 2 illustrates a transverse cross section of the compression assembly of FIG. 1, taken along line 2-2.

DETAILED DESCRIPTION OF THE PREFERRED EMBODIMENTS

Figure 3:
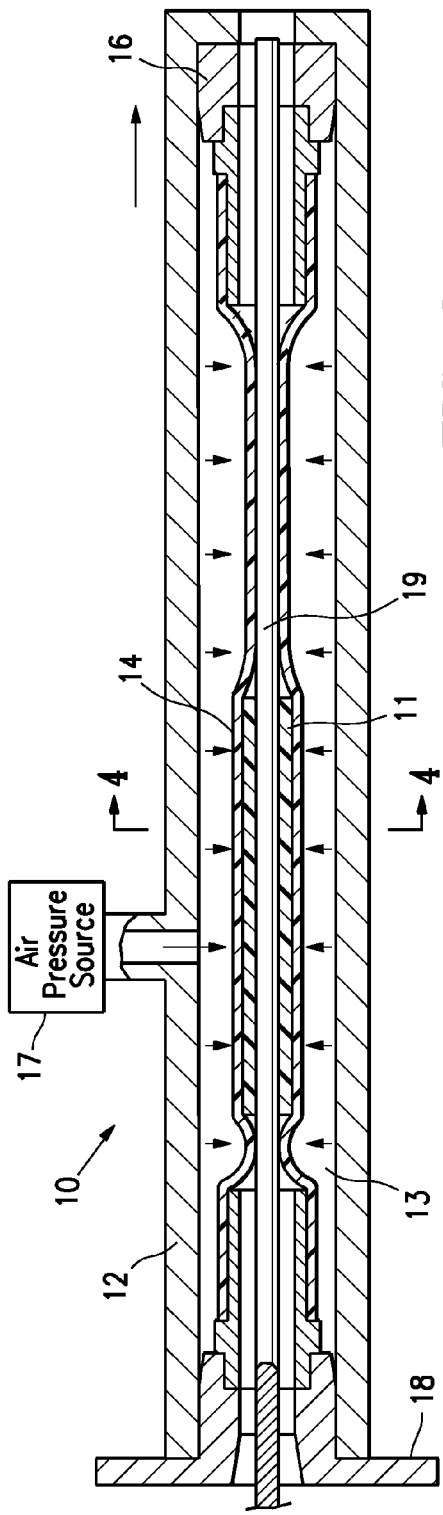
FIG. 3 illustrates a longitudinal cross section of the compression assembly of FIG. 1, with the tube longitudinally stretched to a stretched configuration.

FIG. 1 illustrates a compression assembly 10 found useful in an embodiment of the method of the invention for longitudinally compressing a polymeric tubular layer 11 of a medical device or component thereof. In the embodiment of FIG. 1, the compression assembly 10 comprises a housing 12 having an interior chamber 13 configured to receive a tube 14 therein. A piston 16 which is at one end of the housing 12 is connected to a first end of the tube 14. Piston 16 can be moved back and forth, to thereby longitudinally stretch the tube 14 to a stretched configuration and allow the tube 14 to retract back to a nonstretched configuration. A pressurized fluid source 17 is connected to the housing, to deliver pressurized fluid to the housing interior chamber 13. In the illustrated embodiment, the pressurized fluid source is pressurized air, although a variety of suitable fluids can be used including a liquid such as water. The orifice of a flange 18 at one end of the housing is configured to allow the polymeric tubular layer 11 and a mandrel 19 therein to be introduced into the interior chamber 13 of the housing 12.

FIG. 1 illustrates the polymeric tubular layer 11 on mandrel 19 within the lumen of the tube 14, with the tube 14 in a nonstretched (relaxed) configuration, and without fluid pressure from source 17 on the tube. As best shown in FIG. 2, illustrating a transverse cross section of the assembly of FIG. 1 taken along line 2-2, the inner diameter of the tube in the relaxed configuration is larger than the outer diameter of the polymeric tubular layer 11. The resulting gap between the tube 14 and polymeric tubular layer 11 is preferably minimized, to allow for slidably disposing the polymeric tubular layer 11 within the lumen of the tube 14 yet facilitate pressing the tube down onto the outer surface of the polymeric tubular layer 11 as discussed in more detail below. In one embodiment, the gap is about 0.004 to about 0.006 inches. The relative size of the gap may be somewhat exaggerated in FIG. 2 for ease of illustration.

Figure 4:
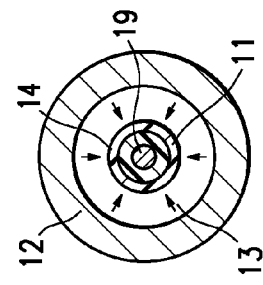
FIG. 4 illustrates a transverse cross section of the compression assembly of FIG. 3, taken along line 4-4.

With the polymeric tubular layer 11 in position within the lumen of the tube 14, the piston 16 is moved outwardly to longitudinally stretch the tube 14 to a stretched configuration. The amount that the tube 14 is stretched depends on the nature of the polymer forming the tube 14, and is typically about 120% or more. In one embodiment, the tube 14 is stretched at least about 150%. Pressurized fluid is delivered from source 17 into the interior chamber 13 of housing 12, to press the tube 14 in the stretched configuration against the polymeric tubular layer 11. In a presently preferred embodiment, the pressurized air is delivered at a pressure of about 100 to about 200 psi. However, a variety of suitable air pressures may be used depending on factors such as the nature of the tube 14. The air pressure enhances the grip between the tube 14 and the polymeric tubular layer 11 to releaseably attach the two together, with the tube radially restraining the polymeric tubular layer 11 therein. The pressurized air forces the tube 14 against the entire length of the polymeric tubular layer 11. FIG. 3 illustrates the tube 14 in a longitudinally stretched configuration, with pressurized air from source 17 pressing the tube 14 radially inward. FIG. 4 illustrates a transverse cross section of the assembly of FIG. 3, taken along line 4-4.

Figure 5:
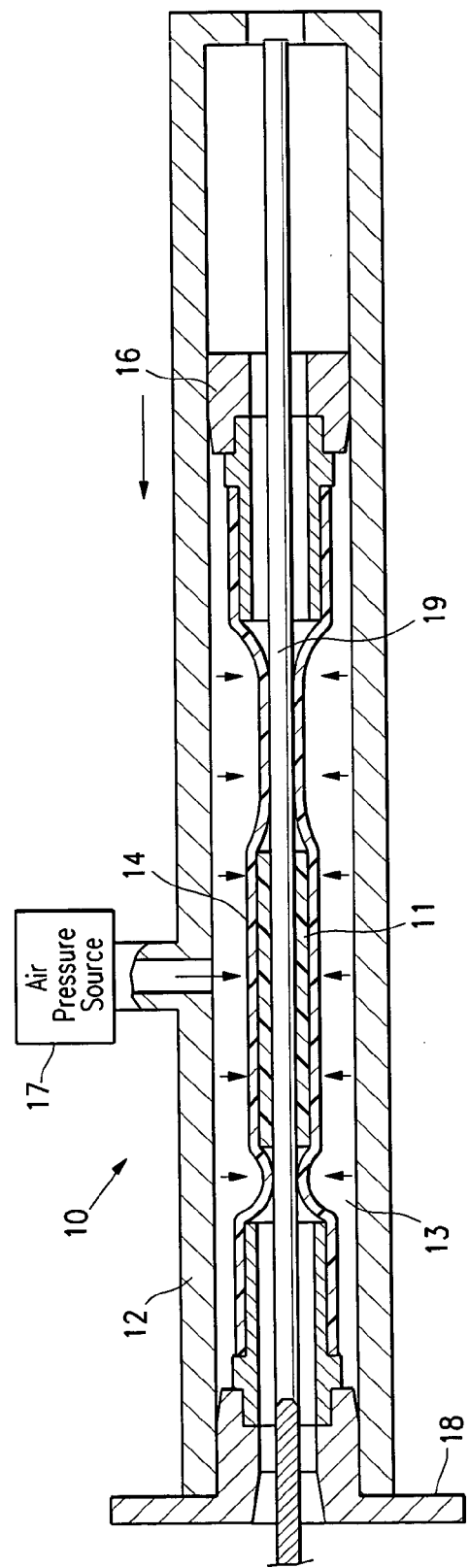
FIG. 5 illustrates a longitudinal cross section of the compression assembly of FIG. 3, with the polymeric tubular layer longitudinally compressed after the tube is released from the stretched configuration.

The polymeric tubular layer 11 is then longitudinally compressed by unrestraining the tube 14 from the stretched configuration. FIG. 5 illustrates the assembly of FIG. 3 after the piston 16 has been moved to unrestrain or release the tube 14 from the stretched configuration but with the pressurized air from air pressure source 17 still forcing the tube 14 radially inward against the layer 11. As the tube 14 retracts from the stretched to the nonstretched configuration, the length of the tube 14 decreases and thereby decreases the length of the polymeric tubular layer 11 by longitudinally compressing the polymeric tubular layer 11. The longitudinally compressed polymeric tubular layer ii illustrated in FIG. 5 can then be removed from the housing 12 after the pressurized air from air pressure source 17 is turned off, or alternatively, before being removed from the housing 12 it can be compressed one or more additional times (e.g., 3 to 4 times) if a higher percent compression is desired. The resulting compressed polymeric tubular layer 11 is removed from the housing 12 by, for example, being forced out through the orifice of flange 18 by pressurized air connected to the opposite end of the housing. In one embodiment, the compression assembly 10 is at room temperature throughout the illustrated stages of FIGS. 1-5, so that the polymeric tubular layer 11 and tube 14 are not heated to elevated temperatures in the stretched or compressed configurations thereof within housing 12. In one embodiment, the polymeric tubular layer 11 is heated to elevated temperatures in the compressed configuration after being removed from the housing 12. For example, in one embodiment, after being removed from housing 12 a compressed ePTFE polymeric tubular layer 11 is heated at about 250°C while being radially restrained.

The resulting compressed polymeric tubular layer 11 preferably has a uniform percent compression along the length thereof. The uniform compression can be determined by providing markings equally spaced apart along the length of the polymeric tubular layer 11 which will move closer together by an equal amount along the length of the polymeric tubular layer 11 if the polymeric tubular layer 11 is uniformly compressed. The compressed polymeric tubular layer 11 is preferably substantially free of wrinkles, i.e., with a uniform outer and inner diameter along the length thereof within normal manufacturing tolerances for a polymeric tubular layer.

In a presently preferred embodiment, the tube 14 is an elastomeric polymer. For example, in one embodiment the tube 14 is an elastomeric polyurethane. In one embodiment, the tube 14 is a high temperature material such as Viton® which can be heated to elevated temperatures of over 400°F. to heat treat the compressed polymeric tubular layer 11 therein. The polymer of the tube 14 generally has a percent elongation of about 40% to about 300%, more specifically about 40% to about 100%. A percent elongation of 100% or less is typically sufficient to allow for stretching the tube 14 without plastic deformation. As the tube 14 longitudinally stretches, the inner diameter of the tube 14 typically decreases. However, it is preferable to avoid decreasing the inner diameter of the tube 14 to the point of contact with the polymeric tubular layer 11 therein during stretching. As a result, the tube 14 having a relatively high percent elongation is typically not required.

Figure 3A:
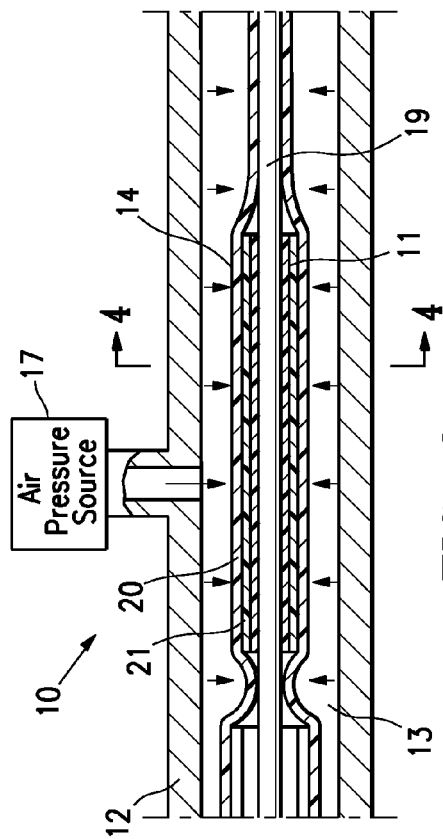
FIG. 3A illustrates an embodiment in which the tube has two layers of different polymeric materials.

In the illustrated embodiment, the tube 14 is a single layered tube. However, in alternative embodiments, the tube 14 has two or more layers of different polymeric materials (see FIG. 3A in which tube 14 has a first layer 20 and a second layer 21). For example, in one embodiment, tube 14 has an outer layer of a first polymer, and an inner layer extending at least along the length of the polymeric tubular layer and formed of a second polymer having a higher coefficient of friction than the outer layer. Thus, the second (inner layer) polymer enhances the frictional attachment of the tube 14 to the polymeric tubular layer 11. The nature of the first (outer layer) polymer is typically chosen to provide other required characteristics such as a high resistance in the axial direction, to thereby provide the multilayered tube 14 with the desired high compressing force/elastic energy in the axial direction during retraction from the stretched configuration. The second (inner layer) polymer can extend the entire length of the tube 14, or preferably extends only along the length of the polymeric tubular layer 11, so that it does not extend along exposed sections of the mandrel 19 at either end of the polymeric tubular layer 11, to thereby minimize frictional forces between the tube 14 and the mandrel along which it must slide during stretching and retraction.

The tube 14 wall thickness is typically minimized, while still being sufficiently thick to prevent or inhibit the tube from buckling or folding under the strain forces encountered during use of the tube in the method of the invention. The tube 14 wall thickness is typically about 0.5 to about 10 mm.

The mandrel 19 is typically a metallic material such as nitinol (NiTi), or stainless steel, although a variety of suitable materials may be used including polymeric materials. The mandrel 19 typically has a lubricious coating to facilitate sliding the polymeric tubular layer 11 and tube 14 on the mandrel 19. In one embodiment, additional polymeric lubricious coatings or sheaths (not shown) are provided on the mandrel along all or part of the length of the mandrel. For example, the lubricious coatings or sheaths (not shown) may extend between the polymeric tubular layer 11 and the mandrel 19, or only on sections of the mandrel located longitudinally adjacent to either end of the polymeric tubular layer 11 (i.e., not between the polymeric tubular layer 11 and the mandrel 19).

The polymeric tubular layer 11 is typically a porous polymeric material, such as expanded polytetrafluoroethylene (ePTFE), an ultra high molecular weight polyolefin including ultra high molecular weight polyethylene, porous polyolefins including polyethylene and polypropylene, or porous polyurethane. In one embodiment, the porous material has a node and fibril microstructure. ePTFE and ultra high molecular weight polyethylene (also referred to as "expanded ultra high molecular weight polyethylene") typically have a node and fibril microstructure, and are not melt extrudable. The node and fibril microstructure, when present, is produced in the porous material using conventional methods, and the polymeric tubular layer 11 of porous polymeric material preferably has the desired microstructure (e.g., porous and/or node and fibril) before being longitudinally compressed in the method of the invention. However, a variety of suitable polymeric materials can be used to form polymeric tubular layer 11 in the method of the invention including conventional catheter balloon materials which are melt extrudable. In one presently preferred embodiment, the porous polymeric material cannot be formed into a polymeric tubular layer of a balloon by conventional balloon blow molding of a tubular extrudate, and is formed into a tube by bonding a sheet of the porous polymeric material together to form polymeric tubular layer 11. For example, the polymeric tubular layer 11 formed of a porous ePTFE polymeric material is typically formed by wrapping a sheet of porous polymeric material on a mandrel and heating the wrapped sheet to fuse sections of the sheet together.

Figure 6:
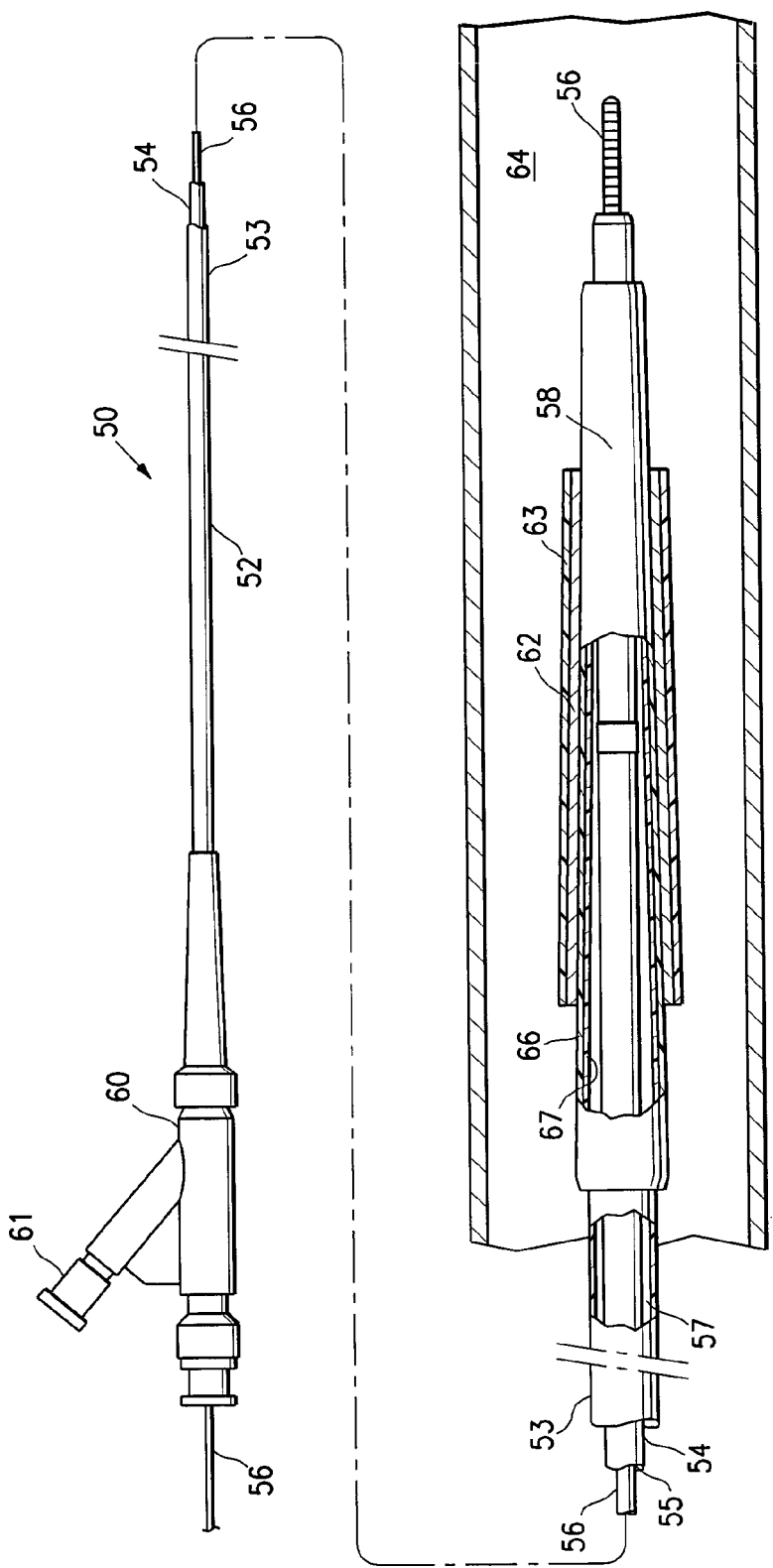
FIG. 6 illustrates a stent delivery balloon catheter having a balloon with a polymeric tubular layer formed according to a method embodying features of the invention.

In a presently preferred embodiment, the polymeric tubular layer 11 is used to form a catheter balloon. FIG. 6 illustrates a balloon catheter having a balloon formed by a method which embodies features of the invention. In the embodiment of FIG. 6, the catheter 50 is an over-the-wire type stent delivery balloon catheter, generally comprising an elongated catheter shaft 52 having an outer tubular member 53 and an inner tubular member 54. Inner tubular member 54 defines a guidewire lumen 55 configured to slidingly receive a guidewire 56, and the coaxial relationship between outer tubular member 53 and inner tubular member 54 defines annular inflation lumen 57. An inflatable balloon 58 disposed on a distal section of catheter shaft 52 has a proximal skirt section sealingly secured to the distal end of outer tubular member 53 and a distal skirt section sealingly secured to the distal end of inner tubular member 54, so that its interior is in fluid communication with inflation lumen 57. An adapter 60 at the proximal end of catheter shaft 52 is configured to provide access to guidewire lumen 55, and to direct inflation fluid through arm 61 into inflation lumen 57. FIG. 6 illustrates the balloon 58 prior to complete inflation, with an expandable stent 62, having a tubular cover 63 thereon, mounted on a working length of the balloon 58. The distal end of the catheter may be advanced to a desired region of a patient's body lumen 64 in a conventional manner, and balloon 58 inflated to expand the covered stent 62, and the balloon deflated, leaving covered stent 62 implanted in the body lumen 64.

In the embodiment illustrated in FIG. 6, balloon 58 has a first layer 66 and a second layer 67 with at least one of the layers 66, 67 being the compressed polymeric tubular layer 11 formed according to the method of the invention. In a presently preferred embodiment, the compressed polymeric tubular layer 11 forms the balloon first layer 66, and comprises a fluoropolymeric material. In one embodiment the fluoropolymeric material is a porous fluoropolymeric material, and preferably a microporous fluoropolymeric material having a node and fibril microstructure such as ePTFE. Although discussed below in terms of one embodiment in which the balloon first layer 66 is formed of ePTFE, it should be understood that in other embodiments the first layer may comprise other materials. The balloon second layer 67 is preferably formed of an elastomeric material, including polyurethane elastomers, silicone rubbers, dienes, styrene-butadiene-styrene block copolymers, polyamide block copolymers, and the like. In a preferred embodiment, layer 67 is an inner layer relative to layer 66, although in other embodiments it may be an outer layer. Layer 67 formed of an elastomeric material limits or prevents leakage of inflation fluid through the microporous ePTFE to allow for inflation of the balloon 58, and expands elastically to facilitate deflation of the balloon 58 to a low profile deflated configuration. The elastomeric material forming layer 67 may consist of a separate layer which neither fills the pores nor disturbs the node and fibril structure of the ePTFE layer 66, or it may at least partially fill the pores of the ePTFE layer 66.

The polymeric tubular layer 11 compressed according to the method of the invention is typically further processed before and after being longitudinally compressed, in order to form layer 66 of balloon 58. For example, in one embodiment, the polymeric tubular layer 11 formed of ePTFE is longitudinally stretched and sintered (i.e., heated) before being longitudinally compressed, and is sintered again after being longitudinally compressed. The longitudinally compressed polymeric tubular layer 11 can optionally be heat treated before or after it is removed from tube 14, to thermally set the compressed dimensions. If not heat treated while being physically restrained on the mandrel 19 by tube 14 or another outer tube, it will generally increase in length by about 0.5% to about 5%. The resulting layer 66 of balloon 58 preferably has a desired dimension, and dimensional stability (i.e., minimal changes in length occurring during inflation).

The dimensions of catheter 50 are determined largely by the size of the balloon and guidewires to be employed, catheter type, and the size of the artery or other body lumen through which the catheter must pass or the size of the stent being delivered. Typically, the outer tubular member 53 has an outer diameter of about 0.025 to about 0.04 inch (0.064 to 0.10 cm), more specifically about 0.037 inch (0.094 cm), and a wall thickness of about 0.002 to about 0.008 inch (0.0051 to 0.02 cm), more specifically about 0.003 to 0.005 inch (0.0076 to 0.013 cm). The inner tubular member 54 typically has an inner diameter of about 0.01 to about 0.018 inch (0.025 to 0.046 cm), more specifically about 0.015 to about 0.016 inch (0.038 to 0.04 cm), and a wall thickness of 0.002 to 0.005 inch (0.005 to 0.013 cm). The overall working length of the catheter 50 may range from about 100 to about 150 cm, and is typically about 143 cm. The balloon 58 typically has a length of about 0.5 cm to about 6 cm, and an inflated working diameter of about 2 to about 10 mm.

Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 6 is an over-the-wire stent delivery catheter, the catheter may comprise other types of intravascular catheters, such as a rapid exchange balloon catheter. Rapid exchange catheters generally comprise a distal guidewire port in a distal end of the catheter, a proximal guidewire port in a distal shaft section and typically spaced a substantial distance from the proximal end of the catheter, and a short guidewire lumen extending between the proximal and distal guidewire ports in the distal section of the catheter.

A compressed polymeric tubular layer 11 for a layer of a catheter balloon was formed according to the following example. A polymeric tubular layer comprising a heat fused wrapped sheet of ePTFE was placed on a lubriciously coated NiTi mandrel, and positioned in the lumen of an elastomeric polyurethane tube in the interior chamber of a housing. The ePTFE polymeric tubular layer had a length of about 80 mm, an inner diameter of about 0.8 mm and an outer diameter of about 1 mm. The polyurethane tube had a length of about 80 mm, an inner diameter of about 1.5 mm and an outer diameter of about 5 mm. With the ends of the polyurethane tube attached to a piston, the piston was moved outwardly to stretch the polyurethane tube to a stretched configuration having a length of about 120 mm (i.e., stretched about 150%). Pressurized air was then delivered into the housing interior chamber through an intermediate port between the two ends of the housing at a pressure of about 200 psi, which applied a radially inward force on an outer surface of the polyurethane tube. The piston was then moved back inwardly to the starting position, thus allowing the polyurethane tube to retract to a nonstretched configuration, and thus longitudinally compressing the ePTFE polymeric tubular layer. The ePTFE polymeric tubular layer was compressed to a length of about 50 mm (i.e., about 35% compression). The pressurized air source was disconnected and the pressure inside the housing chamber allowed to return to room pressure. Pressurized air connected to one end of the housing forced the compressed ePTFE polymeric tubular layer and the mandrel out of the lumen of the tube and through the opposite end of the housing, and the compressed ePTFE polymeric tubular layer was slid off the mandrel, to form the compressed ePTFE polymeric tubular layer. The polyurethane tube is intact (i.e., not cut or torn during removal) and remained in the housing, ready to perform additional compressions. The compressed ePTFE polymeric tubular layer was not heat treated in the compressed configuration before being removed from the polyurethane tube, and after being heated to thermally set the compressed dimensions at about 400° F., it had a final length of about 52 mm, for a final percent compression of about 33%. The compressed polymeric tubular layer had an inner diameter of about 0.8 mm and an outer diameter of about 1 mm, and was substantially free of wrinkles along the tube surface.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment, and not in other embodiments, it should be apparent that individual features of one embodiment may be combined with one or more features of another embodiment or features from a plurality of embodiments.

What is claimed is:

1. A method of making a polymeric tubular layer of an expandable medical device or component, comprising:
   a) placing a polymeric tubular layer having a length in a lumen of a tube, with the polymeric tubular layer in the lumen of the tube being disposed on a mandrel, and the tube and polymeric tubular layer being in a housing;
   b) longitudinally stretching the tube to a stretched configuration and restraining the tube in the stretched configuration;
   c) attaching the tube in the stretched configuration to the polymeric tubular layer by exposing the tube with the polymeric tubular member therein to a pressurized fluid introduced into the housing, to thereby apply a radially inward force to the tube;
   d) unrestraining the tube to release the tube from the stretched configuration so that the length of the tube decreases and thereby longitudinally compresses the polymeric tubular layer;
   e) detaching the tube from the compressed polymeric tubular layer; and
   f) removing the compressed polymeric tubular layer from the lumen of the tube and from the mandrel, to form the polymeric tubular layer of the expandable medical device.

2. The method of claim 1 wherein the pressurized fluid is air introduced into the housing at a sufficient pressure to radially restrain the polymeric tubular layer, so that the longitudinally compressed polymeric tubular layer is substantially free of wrinkles.

3. The method of claim 1 wherein the pressurized fluid is air introduced into the housing at a pressure of about 100 to about 200 psi.

4. The method of claim 1 wherein the tube comprises a polymer having a higher resistance in the axial direction than in the radial direction, and the pressurized fluid is air introduced into the housing at a pressure of about 100 to about 200 psi.

5. The method of claim 1 wherein the tube comprises an elastomeric polymer and the elastomeric polymer tube is stretched at least about 120%.

6. The method of claim 1 wherein the tube comprises an outer layer of a first polymer, and an inner layer extending at least along the length of the polymeric tubular layer and formed of a second polymer having a higher coefficient of friction than the outer layer first polymer.

7. The method of claim 1 including repeating b), c), d), and e) one or more times before f).

8. The method of claim 1 wherein the polymeric tubular layer is compressed uniformly along the length thereof to a final percent compression of about 30% to about 65%.

9. The method of claim 1 wherein the polymeric tubular layer comprises a porous polymer selected from the group consisting of expanded polytetrafluoroethylene and ultra high molecular weight polyethylene, and including heating the compressed polymeric tubular layer after removal from the tube lumen.

10. The method of claim 1 wherein the mandrel has lubricious sheaths thereon longitudinally adjacent to either end of the polymeric tubular layer, and removing the compressed polymeric tubular layer from the lumen of the tube comprises pushing or pulling the compressed polymeric tubular layer and the mandrel from the lumen of the tube.

11. The method of claim 1 wherein the tube is not cut or torn during removal of the compressed polymeric tubular layer in f).

12. A method of making a catheter having a balloon with at least one polymeric tubular layer, comprising:
 a) placing a polymeric tubular layer having a length in a lumen of a tube, with the polymeric tubular layer in the lumen of the tube being disposed on a mandrel, and the tube and polymeric tubular layer being in a housing;
 b) longitudinally stretching the tube to a stretched configuration and restraining the tube in the stretched configuration;
 c) attaching the tube in the stretched configuration to the polymeric tubular layer by exposing the tube with the polymeric tubular member therein to a pressurized fluid introduced into the housing, to thereby apply a radially inward force to the tube;
 d) unrestraining the tube to release the tube from the stretched configuration so that the length of the tube decreases and thereby decreases the length of the polymeric tubular layer by longitudinally compressing the polymeric tubular layer;
 f) detaching the tube from the compressed polymeric tubular layer;
 g) removing the compressed polymeric tubular layer from the lumen of the tube and from the mandrel, to form the at least one polymeric tubular layer of the catheter balloon; and
 h) securing the catheter balloon polymeric tubular layer to a catheter shaft, to form the balloon catheter.

13. The method of claim 12 wherein the polymeric tubular layer comprises a porous polymer selected from the group consisting of expanded polytetrafluoroethylene and ultra high molecular weight polyethylene, and including securing an elastomeric tubular layer to the compressed polymeric tubular layer after g), so that the catheter balloon is a multilayered catheter balloon.

14. A method of making a polymeric tubular layer of an expandable medical device or component, comprising:
 a) placing a polymeric tubular layer having a length in a lumen of a tube, with the polymeric tubular layer in the lumen of the tube being disposed on a mandrel, and the tube comprises an outer layer of a first polymer, and an inner layer extending at least along the length of the polymeric tubular layer and formed of a second polymer having a higher coefficient of friction than the outer layer first polymer;
 b) longitudinally stretching the tube to a stretched configuration and restraining the tube in the stretched configuration;
 c) attaching the tube in the stretched configuration to the polymeric tubular layer;
 d) unrestraining the tube to release the tube from the stretched configuration so that the length of the tube decreases and thereby longitudinally compresses the polymeric tubular layer;
 e) detaching the tube from the compressed polymeric tubular layer; and
 f) removing the compressed polymeric tubular layer from the lumen of the tube and from the mandrel, to form the polymeric tubular layer of the expandable medical device.

* * * * *